United States Patent
Rupp

(10) Patent No.: US 10,973,642 B1
(45) Date of Patent: Apr. 13, 2021

(54) HIP JOINT PROSTHESIS

(71) Applicant: Frederick Rupp, Highlands Ranch, CO (US)

(72) Inventor: Frederick Rupp, Highlands Ranch, CO (US)

(*) Notice: Subject to any disclaimer, the term of this patent is extended or adjusted under 35 U.S.C. 154(b) by 0 days.

(21) Appl. No.: 16/812,249

(22) Filed: Mar. 6, 2020

(51) Int. Cl.
A61F 2/32 (2006.01)
A61F 2/36 (2006.01)
A61F 2/34 (2006.01)
A61F 2/30 (2006.01)

(52) U.S. Cl.
CPC .............. A61F 2/32 (2013.01); A61F 2/34 (2013.01); A61F 2/36 (2013.01); A61F 2002/30566 (2013.01)

(58) Field of Classification Search
CPC .. A61F 2002/30289; A61F 2002/30291; A61F 2002/4029; A61F 2/40
See application file for complete search history.

(56) References Cited

U.S. PATENT DOCUMENTS

| | | | |
|---|---|---|---|
| 4,314,381 A * | 2/1982 | Koeneman | A61F 2/30724 623/23.17 |
| 5,011,479 A | 4/1991 | Persson | |
| 5,507,818 A | 4/1996 | McLaughlin | |
| 5,507,823 A | 4/1996 | Walston | |
| 5,514,182 A | 5/1996 | Shea | |
| 2002/0143402 A1 | 10/2002 | Steinberg | |
| 2008/0275558 A1 * | 11/2008 | Clifford | A61B 17/7044 623/20.14 |
| 2011/0264230 A1 | 10/2011 | Herr | |
| 2012/0046754 A1 | 2/2012 | Clifford | |
| 2013/0204387 A1 | 8/2013 | Meridew | |
| 2017/0296347 A1 * | 10/2017 | Chua | A61F 2/30744 |

* cited by examiner

Primary Examiner — Yashita Sharma
(74) Attorney, Agent, or Firm — Kyle W. Rost

(57) ABSTRACT

A hip joint prosthesis is formed of a coil spring having a middle section bounded by first and second opposite ends, with one of the two ends configured as a femoral fixing end and the other of the two ends configured as an acetabular fixing end. A central axis of the coil spring extends between the two opposite ends, providing a freely movable, flexible central coil linking the two ends.

1 Claim, 3 Drawing Sheets

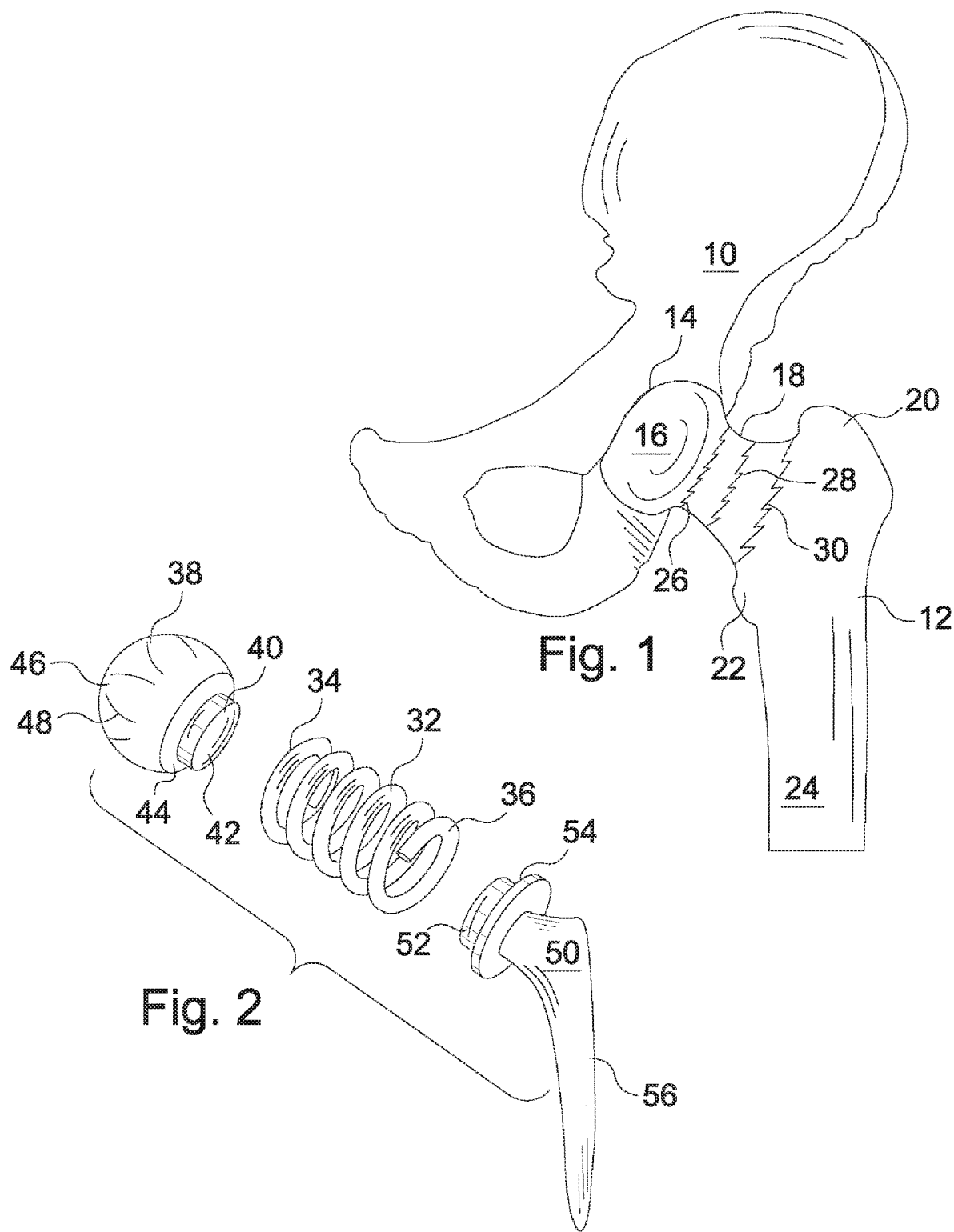

HIP JOINT PROSTHESIS

BACKGROUND OF THE INVENTION

Field of the invention—The invention generally relates to prosthesis and to implantable prosthesis, bone prosthesis, and to joint bone prosthesis. In one aspect, the invention relates to a bone, particularly a joint bone, and more particularly to a hip joint bone, especially to a femoral joint head. In a further aspect, the invention includes a portion of a prosthesis secured to the natural acetabulum by an adhesive or gap filling substance, i.e., cement. The invention also is a substitute for an acetabular cup and femoral head.

Description of Related Art including information disclosed under 37 CFR 1.97 and 1.98—The natural hip joint is a ball-and-socket joint between a ball on the top end of the femur bone of the upper leg and a socket, called the acetabulum, defined in the pelvis. The socket includes cartilage that aids in stabilizing the ball. This area is regarded as a joint capsule. A hip fracture is a break that occurs in the upper part of the femur, such as in the head or neck of the femur. A fracture within the joint capsule is called an intracapsular fracture. The types of breaks in an intracapsular fracture are further categorized. A fracture of the femoral neck, near the femoral head, is further called subcapital. A fracture lower on the femoral neck is called transcervical. Another type of fracture located near the bottom of the femoral neck is known as basicervical and can be regarded as intracapsular. Other types of hip fracture occur below the head and neck of the femur and are not intracapsular.

Treatment of intracapsular fracture in some cases is by hemiarthroplasty, which is replacement of the broken part of the bone with prosthesis. A replacement head is attached to the femur with a metal stem known as a femoral stem that is placed into the hollow center of the femur. The femoral stem may be either cemented into the femur or pressed into this bone. The replacement ball may be either a single unit with integral stem or may be a separate component that is attached to the stem. In either case, the ball is positioned at the upper part of the stem to substitute for the damaged femoral head, which typically has been surgically removed in preparation for implanting the prosthesis. The replacement ball often is formed of a metallic material in hope of surviving wear and tear. However, it is known that even metallic hip prostheses are subject to wearing out, or wearing out adjacent contacted bone.

In other cases, treatment of an intracapsular fracture is by total hip replacement, wherein both the damaged portion of the femur and the cartilage of the acetabulum are surgically removed and replaced. As with the hemiarthroplasty, a replacement head is attached to the femur upon a metal femoral stem that either is pressed or cemented into the hollow center of the femur. For accurate understanding, it may be noted that bone cement is not necessarily an adhesive, but tends to be a fill in gaps between a prosthesis and bone. An example is polymethyl methacrylate (PMMA). The damaged cartilage surface of the acetabulum is removed and replaced with a metal socket. Either screws or bone cement are used to hold the socket in place. A plastic, ceramic, or metal spacer is inserted between the new ball and the socket to serve as a smooth, gliding surface.

Intracapsular replacements using the described replacement heads have been known to fail. Typical causes are loosening implant wear, infection, fracture, and dislocation. For example, after a hip hemiarthroplasty, wear and tear can degrade cartilage in the acetabulum, resulting in painful contact between the metal ball and the exposed bone at the acetabulum. The metal parts of an implant have been known to fail when a plating metal peels off at contact areas. In a general way, these failures are a product of high pressures, impacts, and other difficult conditions encountered by a hip joint prosthesis.

It would be desirable to have a hip joint prosthesis that engages the femur and pelvis in a static relationship such that artificial materials do not slide against one another or against bone of the hip joint.

To achieve the foregoing and other object and in accordance with the purpose of the present invention, as embodied and broadly described herein, the method and apparatus of this invention may comprise the following.

BRIEF SUMMARY OF THE INVENTION

Against the described background, it is a general object of the invention to provide a hip joint prosthesis replacing an enarthrosis or ball-and-socket joint with an artificial flexible element. Such hip joint prosthesis solves the problem of wear-and-tear between elements of a joint prosthesis or between the joint prosthesis and bone or other tissue at the attachment of the prosthesis.

A more specific object of the invention is to create a joint prosthesis that eliminates moving contact between elements of the prosthesis. Where in an ordinary total hip replacement, hip joint prostheses typically have a metallic femoral head that articulates against a metallic or plastic cup or socket. The head bears a great deal of weight and under articulation can degenerate and contribute to degeneration of the socket. The invention reduces or eliminates the articulation to prevent or reduce degeneration of the prosthesis or bone.

Another object of the invention is to create a joint prosthesis that eliminates moving contact between the femoral head of a hip joint prosthesis and the pelvic bone or any other tissue at the attachment of the prosthesis. In an ordinary hemiarthroplasty, a metallic femoral head of the prosthesis is placed to articulate against the acetabulum of the hip bone. Articulation of the head against the bone can degenerate and contribute to degeneration of the bone and cartilage of the acetabulum. The invention reduces or eliminates the articulation formerly common between a femoral head of prosthesis and the acetabulum socket.

A further object is to create a hip joint prosthesis that allows movement between adjacent bones of the hip joint by flex rather than by articulation between surfaces. The typical pivoting ball of a ball-and-socket prosthesis is functionally replaced or eliminated. If a ball is kept as an element of the invention, the ball is repurposed to positionally attach one end of the prosthesis to the acetabulum, preferably in a fixed position without articulation with respect to the acetabulum.

Another object is to provide a prosthesis formed of a coil spring on an elongated central axis, having first and second opposite terminal ends. The two terminal ends fasten the coil spring between the patient's adjacent femur and acetabulum, forming a hip joint prosthesis that allows movement between the hip bone and femur by flex of the coil spring. Replacing a ball-and-socket joint with a prosthesis configured as a coil preserves the original quality of the hip joint as a diarthrosis, capable of freely moving. In addition, the coil provides shock absorption and impact damping, which protect the fixed attachments of the prosthesis to the femur and acetabulum. Such shock absorption and impact damping otherwise tend to be lost when a conventional ball-and-socket prosthesis is used to mend a broken hip. A coil spring prosthesis has the further advantage of being strong and durable, as a preferred material of construction is metal such as steel or titanium, or any other material presently known or hereafter discovered, having suitable qualities for use as a coil spring prosthesis for repairing a broken hip joint.

According to the invention, a hip joint prosthesis is formed of a central coil spring having first and second opposite ends, with one of the two ends configured as a femoral fixing end and the other of the two ends configured as an acetabular fixing end. The central axis of the coil spring extends between the two opposite ends, providing a freely movable, flexible central coil linking the two ends.

The femoral fixing end of the coil may be further joined to a femoral implanting element configured as a femoral stem. One end of the femoral stem is the coil spring attaching end. This end is configured to mate with the femoral fixing end of the coil spring. These two ends may be configured to fit together snugly and may be further secured together by a permanent securement such as a weld. The opposite end of the femoral implanting element is a conventional bone stem configured for insertion into the top end of the intramedullary canal of a surgically prepared femur. The configuration of the stem and the technique of joining of the stem to the femur might be similar to the use of femoral stems in conventional ball-and-socket hip prostheses.

The acetabular fixing end of the coil spring may consist of a winding of the coil spring defining a terminal end of the coil spring axially opposite from the femoral fixing end of the coil spring. The spiral windings of the coil can be sized such that the final spiral loop fits into the surgically prepared acetabulum, thus preparing the acetabular fixing end to be permanently fixed to the acetabulum. Bone cement can be used to fill open areas between the acetabular fixing end and the acetabulum to thereby secure the acetabular fixing end of the coil spring in the acetabulum. The acetabular fixing end of the coil spring can be fabricated in various sizes, diameters, and modifications of pattern to make available a close fit to a selected acetabulum.

According to the invention, a hip prosthesis is formed of a central coil spring having an adhesive head on one end and a bone stem head on the other end, both with nonarticulated connection to the central coil spring.

In a further embodiment, the acetabular fixing end of the coil spring carries a separate end appliance that fits the acetabulum and can be secured therein. For example, the separate fixing appliance can be secured to the acetabulum by screws, bony in-growth, or bone cement. While the separate appliance at the acetabular fixing end of the coil might have a spherical configuration to closely fit a pre-existing shape of the acetabulum or a formed shape of the acetabulum, the appliance is grooved or otherwise configured at surface contact regions with the acetabulum to retain a fixed position in the acetabulum, particularly when fastened by bone cement. The fixing appliance also is secured to the acetabular fixing end of the coil spring. Welding is a suitable for non-articulated securement.

The invention provides free motion to the replaced hip joint by using a one-piece endoprosthesis. A previously typical need for articulation between separate pieces of a hip joint prosthesis is replaced by flex within the coil. The absence of articulation between separate components protects against degeneration of the components and of the bone surfaces.

The accompanying drawings, which are incorporated in and form a part of the specification, illustrate preferred embodiments of the present invention, and together with the description, serve to explain the principles of the invention. In the drawings:

BRIEF DESCRIPTION OF THE SEVERAL VIEWS OF THE DRAWINGS

FIG. 1 is a front view of a left hip and femur, with schematic representations of intracapsular fractures.

FIG. 2 is an isometric, exploded view of the hip joint prosthesis of the invention.

DETAILED DESCRIPTION OF THE INVENTION

Figure 3:
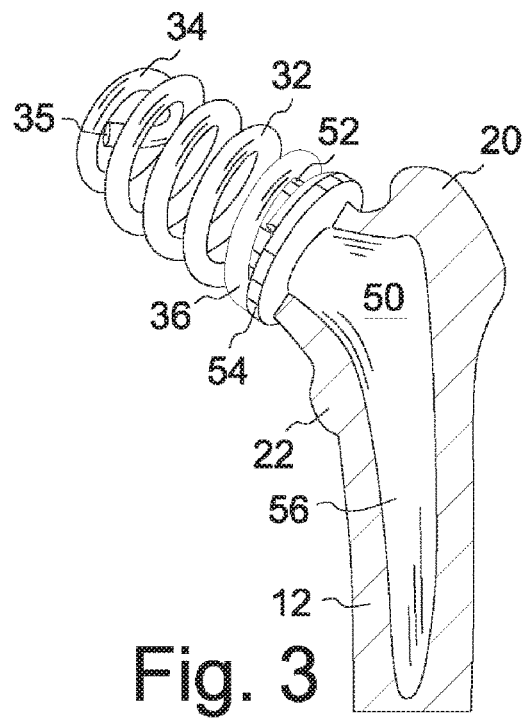
FIG. 3 is an isometric view of the hip joint prosthesis inserted into the femur and with the acetabular fixing end prepared for direct insertion into the acetabulum.

The invention is a hip joint prosthesis that interconnects the acetabulum of the hip bone with the femur using flexing rather than articulation. Articulation is defined as the state of being jointed. Jointed is defined as having joints or jointed segments. Reference to total joint replacement by an artificial joint with a metal femoral ball head operating against an artificial cup is properly called articulation, and this usage is maintained here. Flex or flexation is the action of bending or curving or the condition of being bent or curved. Flex is a motion allowed by bending the material and thus is synonymous with bending load elements such as beams.

The inventive step originates with a novel realization that a prosthesis need not imitate nature. Indeed, imitating nature can be a key source of failure in the efforts of others. Where nature provides a hip joint that is an enarthrosis, trying to copy nature's design of an enarthrosis has led to failures of the imitative hip joint prosthesis. A very understandable cause for this failure is that nature's enarthrosis is living matter with an ability to grow and heal, as well as to biologically lubricate itself and care for itself under shock and load to achieve, in many cases, a lifetime of successful service. A man-made hip joint endoprosthesis suffers the shortcoming of, first, being non-living matter. Articulated portions of a man-made prosthesis may be fabricated of the strongest, hardest materials possible, such as ceramic, steel, or titanium, but they are not alive and the joints made of them can wear out over a short period of use. The present invention uses the novel approach of recognizing that humankind is not capable of fully and truly duplicating nature; and our efforts in that direction are both leading to self-inflicted defects and failing due to non-usage of better available technology that, nevertheless, is non-imitative technology.

With reference to FIG. 1 of the drawings, a typical hip joint is defined between a hip bone 10 and the leg bone known as the femur 12. The hip bone is formed from several smaller bones, which come together to define a socket called the acetabulum 14. Pertinent parts of the femur are a head 16, a neck 18 below the head, a greater trochanter 20, a lesser trochanter 22 located below the neck, and a bone shaft 24 extending below the two trochanters. The area near the head 16 and neck 18 is known as the joint capsule. Fractures of the neck are called intracapsular fractures and are schematically illustrated near the joint capsule of FIG. 1. The types of breaks in an intracapsular fracture are schematically illustrated according to position. A fracture of the femoral neck, near the femoral head, is referred to as subcapital 26. A fracture lower on the femoral neck is referred to as transcervical 28. Another type of fracture located near the bottom of the femoral neck is known as basicervical 30 and sometimes is regarded as intracapsular. Other types of hip fracture occur below the head and neck of the femur and are not intracapsular but may be trochanteric. Intracapsular fractures typically are repaired using a capsule prosthesis of the type employing a ball-and-socket joint.

Conventionally, treatment of intracapsular fracture in some cases is by hemiarthroplasty, which is replacement of the broken part of the bone with a prosthesis. A replacement head is attached to the femur with a metal stem known as a femoral stem that is placed into the hollow center of the femur. The femoral stem may be either cemented into the femur or pressed into this bone. The replacement ball may be either a single unit with integral stem and head or may be a separate stem and separate head that are assembled into a combined stem and head. In either case, the ball is positioned at the upper part of the stem to substitute for the damaged femoral head, which typically has been surgically removed along with preparation of the femur for implanting the prosthesis. The replacement ball often is formed of a metallic material in hope of surviving wear-and-tear. However, it is known that even metallic hip prostheses are subject to wearing out, or wearing out adjacent contacted bone.

In other cases, treatment of an intracapsular fracture is by total hip replacement, wherein both the damaged portion of the femur and the cartilage of the acetabulum are surgically removed and replaced. As with hemiarthroplasty, a replacement head is attached to the femur upon a metal femoral stem that either is pressed or cemented into the hollow center of the femur. For accurate understanding, it may be noted that bone cement is not necessarily an adhesive, but tends to be more similar to a grout that solidifies when placed in gaps between a prosthesis and bone. An example of bone cement is polymethyl methacrylate (PMMA), which is a resin producing a hard, glass-like substance. The damaged cartilage surface of the acetabulum is removed and replaced with a metal socket. Either screws or bone cement are used to hold the socket in place. A plastic, ceramic, or metal spacer is inserted between the new ball and the socket to serve as a smooth, gliding surface.

Figure 4:
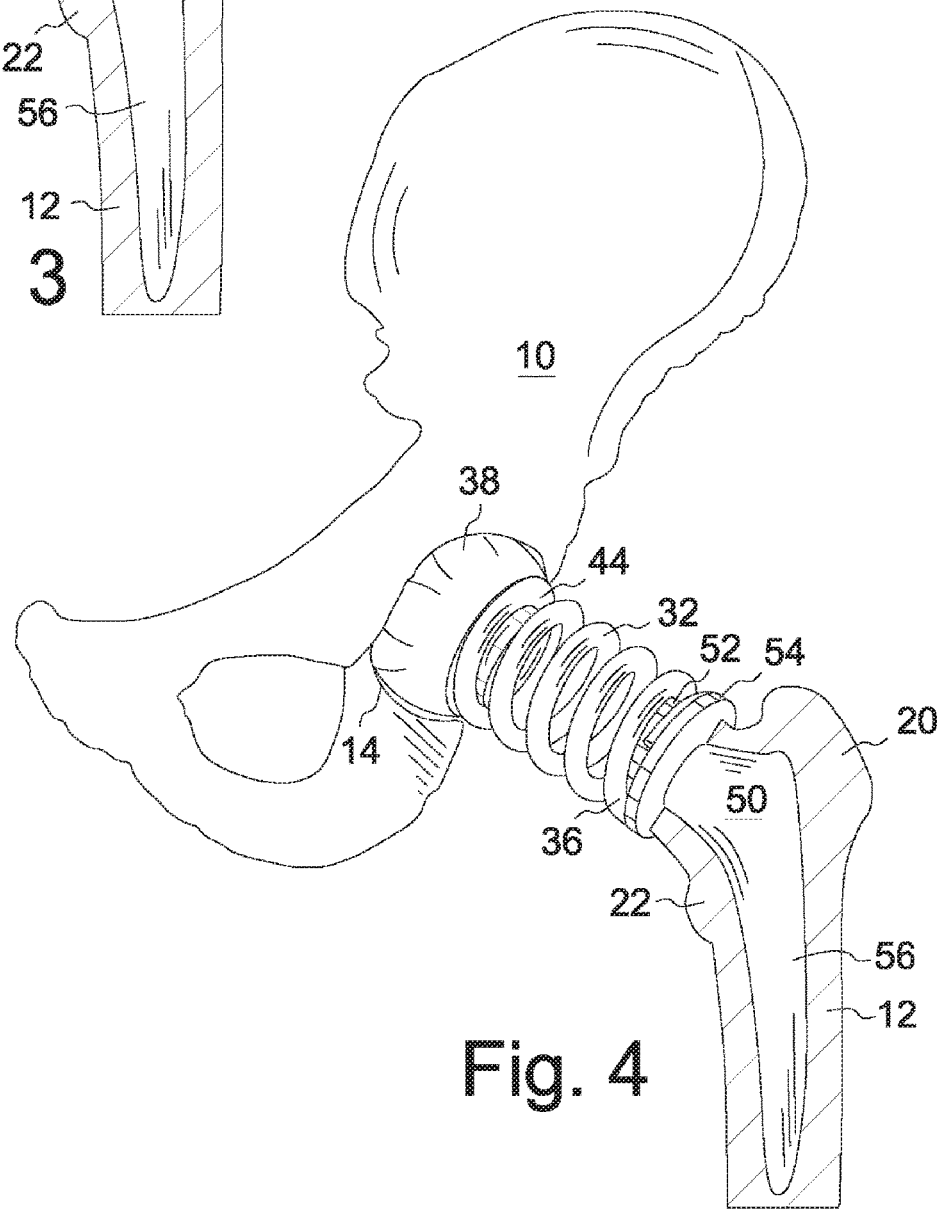
FIG. 4 is an isometric view of the hip joint prosthesis of FIG. 3, inserted in a left hip.

With reference to FIGS. 2-4 of the drawings, the invention provides a new type of prosthesis and implanting surgical procedure. The invention eliminates the need to replace of the femoral ball 16 with a ball prosthesis, which was referred to in prior art as hemiarthroplasty. The invention eliminates the need to replace both the acetabulum 14 and the femoral head 16, which was referred to in prior art as total hip arthroplasty (THA). Instead, the femoral head 16 and any selected portions of neck 18 are removed and replaced by a coil spring 32. A coil spring is a mechanical device made of elastic material formed into the shape of a helix. According to one function, a coil spring is able to store energy by changing length from what can be considered to be a natural length in the application where used. The stored energy is released by reversing the change of length. A coil spring also is able to absorb shock by changing length or configuration. Further, a coil spring can be loaded in order to maintain a force between contacting surfaces. When the force is unloaded, the coil spring will return to its natural length.

A compression spring is a suitable choice, although not the exclusive choice, for a type of spring to be used in a hip prosthesis. A compression spring is an open-coil helical spring that offers resistance to a compressive force applied axially. Usually it is coiled at a constant diameter, although it can be coiled in other needed forms such as conical, concave (barrel), convex (hourglass), or various combinations of these. Compression springs are suited to resist force and store energy, depending upon the application. In a hip prosthesis, a compression spring opposes compression and returns to its uncompressed length when the applied force is removed. To maintain best linearity during deflection, the center 60-80% of the available deflection range of the coil spring is used. In order to implant the coil spring 32, each opposite end of the coil spring is separately considered. The two fixing ends of the coil spring may encompass the first and last 15-20% of the length of the coil.

According to the invention, a coil spring is formed to have a central length 32 and opposite ends. The opposite ends of the coil spring 32 are to be attached between the hip bone and to the femur. The axial end 34 of the coil spring 32 is referred to as an acetabular fixing end. One method of fixing end 34 to the acetabulum is by directly applying the end 34 into the acetabulum. The applied coil spring end 34 can be secured to the acetabulum by a mechanical fastener. Screws are a suitable type of mechanical fastener and can be inserted through a diametric bore in the end coil and then into bone lining the acetabulum. Also, the applied coil spring can be secured to the acetabulum by a chemical fastener. Surgical cement is a suitable type of chemical fastener. It is applied between the end coil of the coil spring and the acetabulum to secure the end of the coil spring in the acetabulum. With either a mechanical fastener or a chemical fastener, complementary sizing and configuration of coil spring end 34 causes spring end 34 to function as the acetabular fixing end. As previously noted, a coil spring can be made in a variety of preselected sizes and shapes, such as conical, concave (barrel), convex (hourglass), or various combinations of these. The size of a terminal end 34 can be offered over a range of diameters to fit the size of the patient's acetabulum to fix the terminal end 34 of spring 32 in the acetabulum.

The acetabular fixing end 34 might be implanted by fitting together and coordinating the shape of the acetabulum 14 and the acetabular fixing end 34. As best shown in FIG. 3, a fit can be established by custom configuring the end coil 34 of the coil spring 32 to approximately fit into the cup shape of the acetabulum, and then securing the end coil 34 in the acetabulum with bone cement. FIG. 3 shows adaptations of the end coil 34 for direct fitting into the acetabulum. One adaptation is that the coil terminus 35 is twisted to produce a final coil of smaller diameter than the coils in the middle of the spring 32. Another adaptation is that the coil terminus 35 is pulled lengthwise or axially to extend the centerline or the coil spring 32 at the terminus, creating a smaller diameter extension that will have a complementary fit with the semi-spherical cavity of the acetabulum.

Another method of securing coil end 34 to the hip bone is by use of a double faced acetabular implant mounting adapter 38, best shown in FIG. 2. One face 40, which may be an inner face, closely mates with the acetabular fixing end winding 34 of the coil. Optionally, face 40 may provide a fitting 42 that engages closely within the end winding 34 of the coil spring. Fitting 42 may be a core fitting that carries a backstop surface 44 that precisely rests against the end shape of the coil 34 so that there is no tendency of the coil to wobble against the adapter 38. The core and backstop are also suitable to be welded to the end winding 34 of the coil. The second face 46 of the implant mounting adapter 38, which may be an outer end face, may be configured as a partial sphere or other shape sized to fit in the cup shaped cavity of the acetabulum. In various studies, the diameter of the acetabulum has been measured over a range from 51 mm to 60 mm, which provides a suggestion of preselecting popular sizes of the face 46 to be made available. Although the partial sphere 46 may resemble an artificial femoral head, it differs in function. Where an artificial femoral head rotates in the acetabulum, the outer face of partial sphere 46 does not rotate. Instead, outer face 46 has a complementary shape to the acetabulum but is fixedly implanted, such as by bone cement, screws, or other fasteners. A surface treatment such as texture, flats, surface projections, or grooves 48 on face 46 secures the cemented junction against rotation and further ensures that bone cement will permanently implant the sphere 46 in the acetabulum. An advantage of using the mounting adapter 38 is that components can be sized and assembled in advance to achieve best fit.

The opposite end of the coil spring 32 is a femoral fixing end 36. The coil spring is to be attached between the respective bones with fixed, non-articulating junctions so that the wound coils of the coil spring take up free motion from any direction, as well as impact and loading. The ends of the spring are immobile at the bones so that there is no wear-and-tear due to motion on either the bones or the ends of the coil spring. The coil spring 32 is placed as an endoprosthesis but performs independently of the wear-and-tear factors encountered by an implanted femoral head, with or without an implanted cup or shell.

The femoral fixing end 36 of coil spring 32 might be secured to the femur by a supplemental femoral implanting element 50. In one embodiment, an end of element 50 faces the femoral fixing end 36 of the coil spring. Optionally, the end element 50 employs a core fitting 52 that fits in the center of the end winding 36 of axial coil spring 32 and otherwise functions similarly to the previously described core fitting 42 of coil spring end 34. Optionally, a backstop surface 54 behind core 52 may be configured to precisely rest against the shape of coil end 36 in wobble free engagement and to also provide a location for a weld. A portion of femoral implanting element 50 facing the top end of femur 12 may be a conventional bone stem 56 for insertion into the surgically prepared femur 12.

Figure 5:
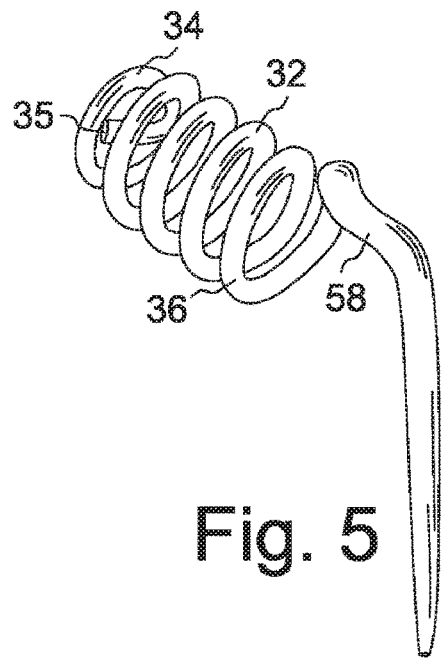
FIG. 5 is an isometric view of a hip joint prosthesis, showing a modified end section of a hip joint prosthesis forming a femur stem.
Figure 6:
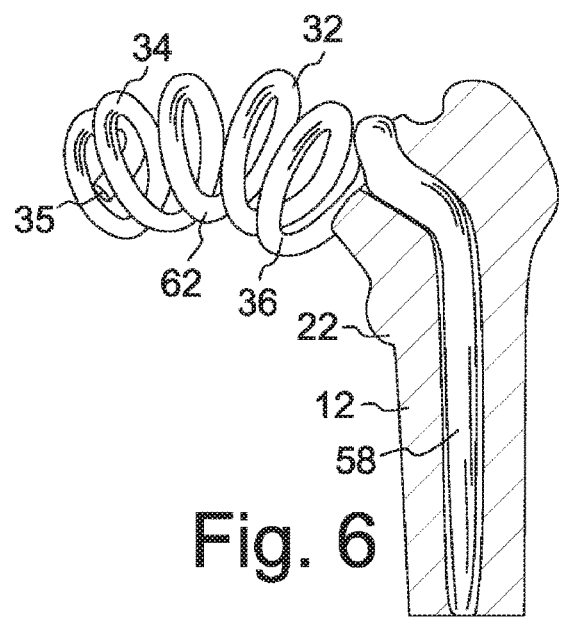
FIG. 6 is an isometric view of a hip joint prosthesis with modified end section installed in a patient's femur and with the coil spring configured in a curve.
Figure 7:
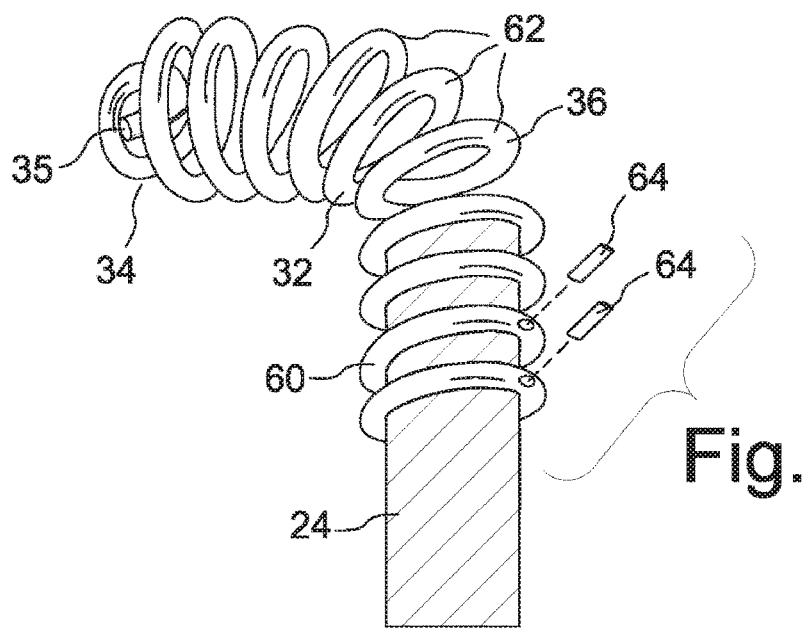
FIG. 7 is an isometric view of a hip joint prosthesis configured in a curve.

With reference to FIGS. 5 and 6, a bone stem or more specifically a femur stem is an accepted fastener to the femur of a hip joint prosthesis. When the prosthesis is a coil spring 32, optional variations in mounting may be preferred that take advantage of the novel characteristics of the coil spring. An optional variation is to extend the length of coil spring 32 at terminus 36, uncoiling or supplementing spring end 36 beyond the ultimate winding 36 to form an added straight spring extension stem 58 that is integral with the coil spring 32. The spring extension stem 58 functions as a femur stem and is inserted into the proximal end of the surgically prepared femur 12.

Another optional variation is to extend the length of the coil spring 32 to configure the end 36 of the coil spring 32 to receive the top of the femur shaft 24 inside an extended coil end 60, so that the coil end 60 jackets the femur shaft 24. Jacketing the femur shaft may require that the longitudinal central axis of the center length of the coil spring 32 is disposed in a curve 62 located between the femur and the acetabulum. A curved spring prosthesis can be prefabricated so that the jacketing coils 60 fit the shaft of the femur. A coil unwinding tool can be applied to the jacketing coils to reduce coil tension while coil spring end 60 is being applied onto the femur. The extended fixing end 60 can be supplementally secured to the femur shaft by penetrating mechanical fasteners 64 such as screws, nails or pins inserted through the helical windings of the jacket coils.

An advantage of using a coil spring on a curved longitudinal axis is compactness of the prosthesis, since a portion of the length of the coil spring 32 is absorbed in the length of the curve 62 due to the non-linear configuration of the curve. The use of a curve has the additional advantage of spreading flex of the coil spring over more coils, which will tend to extend life of the prosthesis. The formation and usage of a curved central length 32 can be applied without limitation to the various described versions of prostheses employing a coil spring. For example, the versions using an integral femur stem 58, illustrated in FIGS. 5 and 6, are readily adaptable. FIG. 6 shows such a curved coil spring in combination with an integral femur stem 58 and coil terminus 35. Further, the invention contemplates that the curve 62 is not limited to prostheses that jacket the femur or employ any particular femur stem. The curve also can be used with acetabular fixing ends 34 such as a terminus coil 35 or an implant mounting adapter 38.

In a surgical procedure to repair a broken hip joint with the coil spring 32, first the desired configuration of the implant is chosen. Where used, the implant mounting adapter 38 is chosen with a pre-installed head 46 of suitable size to fit snugly in the surgically prepared acetabulum 14. Where the implant mounting adapter 38 is not chosen for use, a coil spring 32 is chosen, having an acetabular fixing end that is suitable for implanting in the patient's surgically prepared acetabulum. Either configuration of coil spring is pre-equipped with a femoral implanting element 50. The stem 56 is inserted into the surgically prepared femur as suggested by FIG. 3. The acetabular fixing end of the coil spring is inserted into the surgically prepared acetabulum, with the pre-installed implant mounting adapter 38, when used. Alternative steps in procedure have been mentioned throughout and readily can be substituted into the surgical procedure.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. A prosthetic joint for replacement of the hip joint in a human body, comprising:
   an axially elongated coil spring formed of a series of central coils between first and second opposite ends adapted for fixation, respectively, into an acetabulum socket of the pelvis and into a intramedullary canal of the femur;
   said first end having a semispherical configuration with a diameter in the range from 51 mm to 60 mm for engagement in the acetabulum socket;
   said second end further comprising a bone stem configured for insertion into the top end of the intramedullary canal of a femur;

said coil spring defining a said prosthetic joint providing movement between said first and second opposite ends by flex of the coil spring.

\* \* \* \* \*